United States Patent
Kupa et al.

(10) Patent No.: US 11,278,637 B2
(45) Date of Patent: *Mar. 22, 2022

(54) SYSTEMS AND METHODS FOR INTELLIGENT DISINFECTION OF DISINFECTION ENVIRONMENTS THROUGH USE OF ULTRA-VIOLET LIGHTS

(71) Applicant: Siemens Industry, Inc., Alpharetta, GA (US)

(72) Inventors: Timur Kupa, Crystal Lake, IL (US); Rene Herrera, Brighton, CO (US); Pornsak Songkakul, Mequon, WI (US)

(73) Assignee: Siemens Industry, Inc., Alpharetta, GA (US)

( * ) Notice: Subject to any disclaimer, the term of this patent is extended or adjusted under 35 U.S.C. 154(b) by 286 days.

This patent is subject to a terminal disclaimer.

(21) Appl. No.: 16/026,317

(22) Filed: Jul. 3, 2018

(65) Prior Publication Data
US 2020/0009280 A1    Jan. 9, 2020

(51) Int. Cl.
| | | |
|---|---|---|
| *A61L 2/24* | (2006.01) | |
| *A61L 2/00* | (2006.01) | |
| *A61L 2/10* | (2006.01) | |
| *A61L 9/20* | (2006.01) | |

(52) U.S. Cl.
CPC ............ *A61L 2/24* (2013.01); *A61L 2/0047* (2013.01); *A61L 2/10* (2013.01); *A61L 9/20* (2013.01); *A61L 2202/25* (2013.01)

(58) Field of Classification Search
CPC . A61L 2/24; A61L 2/0047; A61L 2/10; A61L 9/20; A61L 2202/25; A61L 2209/111; A61L 2202/14
See application file for complete search history.

(56) References Cited

U.S. PATENT DOCUMENTS

| | | | | |
|---|---|---|---|---|
| 9,265,678 B2* | 2/2016 | Hill | ............................ | A61L 2/10 |
| 9,700,641 B2* | 7/2017 | Hawkins | ................. | H05B 45/56 |
| 2013/0085609 A1* | 4/2013 | Barker | ................... | G05B 15/02 |
| | | | | 700/276 |

(Continued)

FOREIGN PATENT DOCUMENTS

| | | |
|---|---|---|
| EP | 3 173 960 A1 | 5/2017 |
| WO | 2011/072087 A1 | 6/2011 |

(Continued)

OTHER PUBLICATIONS

PCT Search Report dated Dec. 3, 2019, for PCT Application PCT/US2019/040089, 14 pages.

*Primary Examiner* — Regina M Yoo

(57) ABSTRACT

A building automation system (BAS) may control ultra-violet (UV) lights to intelligently disinfect a disinfection environment (e.g., a patient room). In some examples, the BAS includes a disinfection environment tracking engine and a UV light control engine. The disinfection environment tracking engine may access patient room data indicative of a state of a patient room of a patient, medical data of the patient, the medical data of the patient specifying a medical condition of the patient, real-time location data of the patient. The UV light control engine may control operation of UV lights to disinfect the patient room based on the patient room data, the medical data of the patient, and the real-time location data of the patient.

7 Claims, 7 Drawing Sheets

(56) References Cited

U.S. PATENT DOCUMENTS

2016/0019813 A1* 1/2016 Mullen ................ G16H 20/70
 434/236
2017/0049915 A1* 2/2017 Brais ...................... A61L 2/10
2018/0017947 A1 1/2018 Kupa et al.

FOREIGN PATENT DOCUMENTS

| WO | 2014/022717 A1 | 2/2014 |
| WO | 2015/026407 A1 | 2/2015 |
| WO | 2015/168768 A1 | 11/2015 |

* cited by examiner

SYSTEMS AND METHODS FOR INTELLIGENT DISINFECTION OF DISINFECTION ENVIRONMENTS THROUGH USE OF ULTRA-VIOLET LIGHTS

BACKGROUND

Building systems may be used to control environmental conditions in buildings. Such building systems may benefit from improvements.

SUMMARY

Disclosed implementations include systems, methods, devices, and logic that support intelligent disinfection of disinfection environments through use of ultra-violet (UV) lights.

In one example, a method may be performed, executed, or otherwise carried out by a building automation system (BAS). The method may include accessing patient room data indicative of a state of a patient room of a patient and controlling operation of a UV light to disinfect the patient room based on the patient room data.

In another example, a system may include a disinfection environment tracking engine and a UV light control engine. The disinfection environment tracking engine may be configured to access patient room data indicative of a state of a patient room of a patient; access medical data of the patient, the medical data of the patient specifying a medical condition of the patient; and access real-time location data of the patient. The UV light control engine may be configured to control operation of a UV light to disinfect the patient room based on the patient room data, the medical data of the patient, and the real-time location data of the patient.

In yet another example, a non-transitory machine-readable medium may store instructions executable by a processor. When executed, the instructions may cause the processor or a building automation system to access patient room data indicative of a state of a patient room of a patient, the patient room data including an occupancy schedule for the patient room that indicates an unoccupied time period during which the patient does not occupy the room; access medical data of the patient, the medical data of the patient specifying a medical condition of the patient; and control operation of an UV light to disinfect the patient room based on the patient room data and the medical condition of the data, including by calibrating the UV light to account for a length of the unoccupied time period and a severity of the medical condition of the patient.

BRIEF DESCRIPTION OF THE DRAWINGS

Certain examples are described in the following detailed description and in reference to the drawings.

DETAILED DESCRIPTION

Healthcare associated infections pose a significant issue in modern medical practice. Estimates for annual medical costs arising from healthcare associated infections have surpassed $30 billion (USD) and continue to increase. Mechanisms to address healthcare associated infections include surface cleaning, personal hygiene, and, more recently, UV disinfection through UV lighting. Use of UV lights for UV disinfection (in combination with other medical cleaning processes) can result in marked decreases in healthcare associated infections. However, manual operation of UV lights can be cumbersome and inefficient. UV disinfecting lights also pose safety issues, as inadvertent exposure to UV lighting by patients, medical personnel, or other persons may cause significant bodily harm.

The disclosure herein may provide systems, methods, devices, and logic for intelligent control of UV lights to disinfect patient rooms. As described in greater detail below, a building automation system may track disinfection environments and automate operation of UV lights to disinfect patient rooms. The building automation system may account for any number of various environmental and patient-based factors to intelligently control UV lights, doing so to increase UV light exposure in spaces susceptible to healthcare associated infections (e.g., hospital rooms). Described UV light control features may reduce instances of healthcare associated infections as UV lighting may be more efficiently and effectively operated as compared to manual operation.

As another benefit of the UV light control features described herein, cost savings may be achieved by optimizing operation parameters and activation times of controlled UV lights based on possible infection exposures, available disinfection times, patient-specific issues, etc. Further, the UV light control features described herein may track room occupancy in various ways, whether through occupancy sensors or patient real-time location data, automatically prioritizing safety by deactivating UV light operation upon detection that a disinfection environment is occupied.

These and other features and benefits of UV light control by a building automation system are described in greater detail herein.

Figure 1:
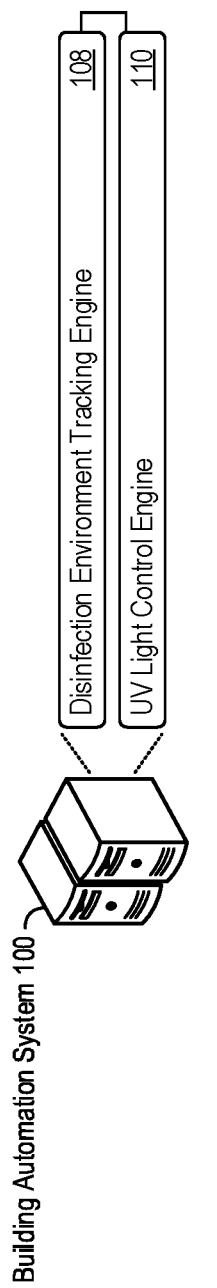
FIG. 1 shows an example of a building automation system that supports intelligent control of UV lights to disinfect any number of disinfection environments.

FIG. 1 shows an example of a building automation system 100 that supports intelligent control of UV lights to disinfect any number of disinfection environments The building automation system 100 may take the form of a computing system, including a single or multiple computing devices such as application servers, compute nodes, desktop or laptop computers, smart phones or other mobile devices, tablet devices, embedded controllers, and more. The building automation system 100 may include any system component that supports the control of building elements, such as heating, ventilation, air condition, lights and blinds, safety features, and any other building equipment. In some implementations, the building automation system 100 implements a unified building automation tool or building automation program through which multiple building controls are integrated, e.g., to increase energy and cost efficiencies, automate building operations, and more.

As described in greater detail herein, the building automation system 100 may support control of UV lights to disinfect disinfection environments of any number or type, e.g., patient rooms. The building automation system 100 may automate the activation and deactivation of UV lights to disinfect patient rooms (or any other disinfection environment) based on tracked environment data, which may include patient room occupancy, patient treatment schedules, medical conditions of patients, real-time location data of patients, any other user-configurable factors, or combinations thereof. In some instances, the UV light control features described herein may provide disinfection of patient rooms with increased frequency or improved efficiency, which may result in a reduction in healthcare associated infections.

As an example implementation, the building automation system 100 shown in FIG. 1 includes a disinfection environment tracking engine 108 and a UV light control engine 110. The building automation system 100 may implement the engines 108 and 110 (and components thereof) in various ways, for example as hardware and programming. The programming for the engines 108 and 110 may take the form of processor-executable instructions stored on a non-transitory machine-readable storage medium and the hardware for the engines 108 and 110 may include a processor to execute those instructions. A processor may take the form of single processor or multi-processor systems, and in some examples, the building automation system 100 implements multiple engines using the same computing system features or hardware components (e.g., a common processor or a common storage medium). The GUI 112 may include various components through which a user interfaces with the building automation system 100, such as a display, keyboard, mouse, touchscreen, etc.

In operation, the disinfection environment tracking engine 108 may track a combination of building environment data and patient data relevant to a disinfection environment, and the UV light control engine 110 may control UV lights based on the tracked data. In a hospital or other healthcare setting, the disinfection environment tracking engine 108 may access patient room data indicative of a state of a patient room of a patient, medical data of the patient that specifies a medical condition of the patient, and real-time location data of the patient. In such examples, the UV light control engine 110 may control operation of a UV light to disinfect the patient room based on the patient room data, the medical data of the patient, and the real-time location data of the patient.

Some example features relating to UV light control are presented in greater detail next. Many of the UV light control features presented herein are described via a patient room as an illustrative disinfection environment. However, a building automation system may consistently implement any of the described UV light control features for other disinfection environments as well, such as hospitality spaces (e.g., hotel rooms), food preparation facilities, cruise ships or other entertainment spaces, school classrooms, mixed office spaces, or any other environment in which UV lighting can be used for disinfection.

Figure 2:
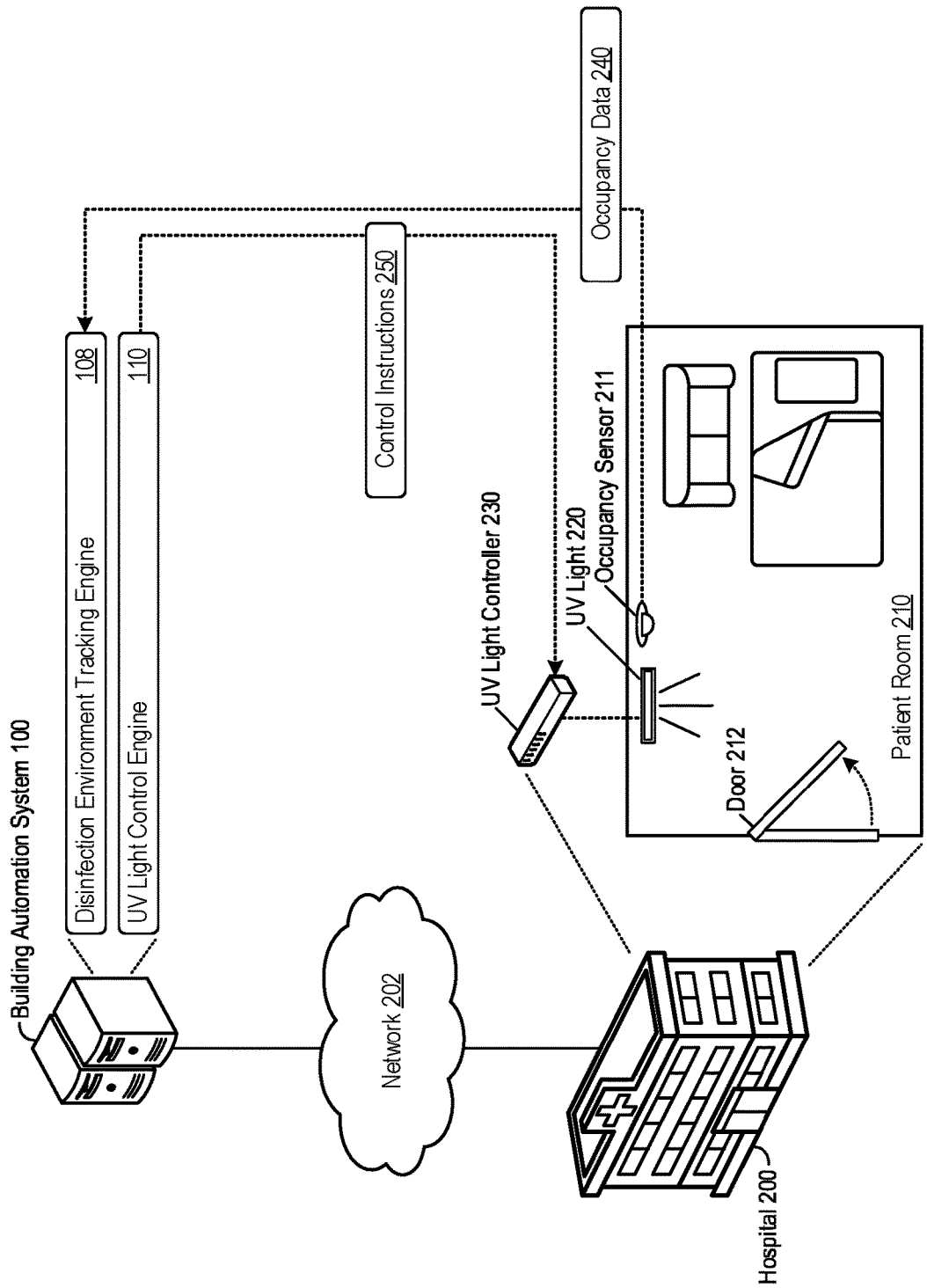
FIG. 2 shows an example of UV light control by a building automation system based on patient room data.

FIG. 2 shows an example of UV light control by a building automation system based on patient room data. The example shown in FIG. 2 includes a building automation system 100 and an example disinfection environment depicted through a hospital 200. Although shown as physically remote to the hospital 200 in FIG. 2, in some examples the building automation system 100 is located within or as part of the hospital 200, whether in part or in whole.

The building automation system 100 may provide control capabilities for various building elements of the hospital 200. Communications between the building automation system 100 and the hospital 200 may be supported by the network 202. The network 202 may take the form of any combination of one or more communication networks (or sub-networks) and supporting components by which the building automation system 100 may interact with specific building elements of the hospital 200. As such, the network 202 may include the Internet, proprietary backend communication systems, building device interfaces, and the like.

In the example shown in FIG. 2, the hospital 200 includes a patient room 210. The patient room 210 may be any physical space assigned to a patient, such as a hospital room, a treatment area, an allocated section of a hospital wing, etc. Accordingly, the patient 210 may include various building elements such as a bed, furniture, medical equipment or devices, lighting and blinds, tables, televisions, etc. In the particular example shown in FIG. 2, the patient room 210 includes a patient bed, a couch, an occupancy sensor 211, a door 212, and a UV light 220. The UV light 220 may be any UV lighting device or building element that supports room disinfection. In that regard, the UV light 220 may provide sterilization capabilities through UV light emanation. Operation of the UV light 220 may be set through a UV light controller 230, which may include any circuitry that controls UV light 220 activation or deactivation, and support configuration of specific settings or characteristics of the emitted UV light (e.g., intensity, frequency, modulation, or any other UV light operation parameters).

The building automation system 100 may support automated operation of the UV light 220 in the patient room 210. In particular, the building automation system 100 may intelligently automate operation of the UV light 220 by communicating activation, parameter configuration, or deactivation instructions to the UV light controller 230. Such instructions may be issued by the building automation system 100 based on room occupancy schedules, other preset schedules, room occupancy states, and other factors, doing so while managing power and energy consumption of the UV light 220 (e.g., by identifying opportunities to reduce excess energy consumption for the disinfection process). In doing so, the building automation system 100 may increase disinfection efficiency, optimize disinfection time, reduce building costs, or provide other benefits.

In some implementations, the building automation system 100 controls operation of the UV light 220 based on occupancy of the patient room 210. To track occupancy, the disinfection environment tracking engine 108 may acquire patient room data for the patient room 210, which may include any data indicative of a state of a patient room of a patient. For instance, the disinfection environment tracking engine 108 may access an occupancy status of the patient room from the occupancy sensor 211 in the patient room 210, whether by polling the occupancy sensor 211 or having occupancy status changes pushed from the occupancy sensor 211. In the example shown in FIG. 2, the disinfection environment tracking engine 108 obtains an occupancy data 240 from the occupancy sensor 211, which may include data indicative of an occupancy state of the patient room 210.

The building automation system 100 may activate the UV light 220 on an opportunistic basis at times (e.g., whenever) the patient room 210 is unoccupied. Based on the occupancy status of the patient room 210, the UV light control engine 110 may activate or deactivate the UV light 220, for instance by issuing activation or deactivation commands to the UV light controller 230. Activation or deactivation commands from the UV light control engine 110 may be included as control instructions, e.g., as depicted in FIG. 2 as the control instructions 250. When the occupancy status indicates the patient room 210 is unoccupied, the UV light control engine 110 may activate the UV light 220 to disinfect the patient room. When the occupancy status accessed from the occupancy sensor 211 indicates the patient room 210 is occupied (whether by the patient or another person), the UV light control engine 110 may deactivate the UV light 220. Accordingly, the UV light control engine 110 may activate the UV light 220 for room disinfection based on a present occupancy status of the patient room 210, e.g., as tracked by the occupancy sensor 211.

In some implementations, the UV light control engine 110 may utilize a determined occupancy status in combination with other factors to control operation of the UV light 220. Some such examples are described next in FIG. 3 with respect to patient schedules and real-time location data of a patient.

Figure 3:
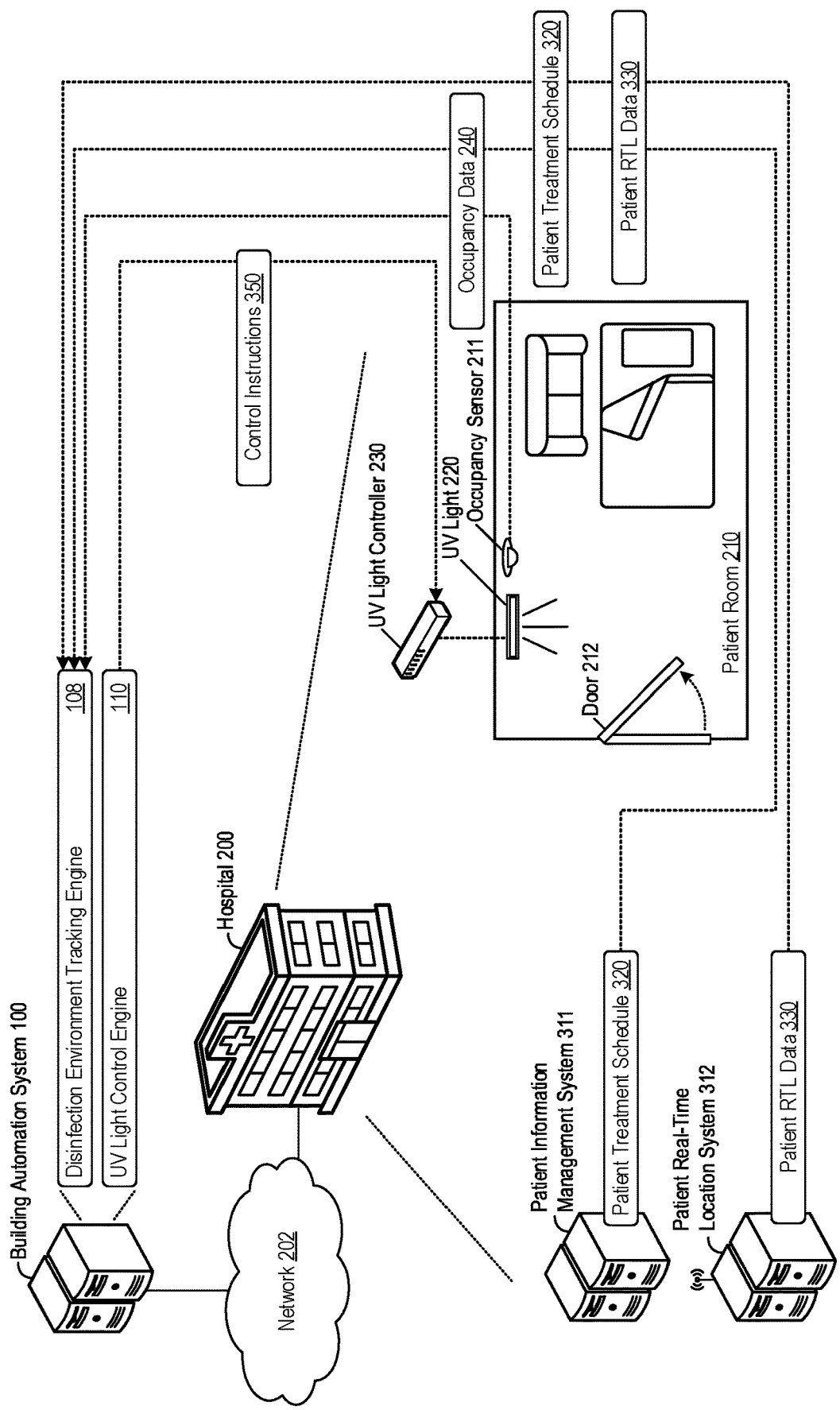
FIG. 3 shows an example of UV light control by a building automation system based on patient room data and real-time location data of a patient.

FIG. 3 shows an example of UV light control by a building automation system 100 based on patient room data and real-time location data of a patient. To support such operation, the disinfection environment tracking engine 108 may access disinfection environment or patient data from various sources to support intelligent control of the UV light 220. As examples, the hospital 200 may include various systems that track relevant patient data that the UV light control engine 110 may utilize to intelligently control UV lighting. In FIG. 3, the hospital 200 includes a patient information management system 311 and a patient real-time location system 312.

The patient information management system 311 may store patient or other medical information of any type. Such patient/medical information may include electronic medical records of patients, disease and treatment history, admission and discharge records, prescription schedules, billing systems, procedural strategies, medical literature systems, disease databases, and more. To support such data warehousing, the patient information management system 311 may itself incorporate or include multiple disparate information systems, including as examples patient admission/discharge/transfer (ADT) systems, patient bed management systems (BMS), billing systems, registration and scheduling systems, occupancy schedules, and more.

The UV light control engine 110 may operate the UV light 220 based on occupancy periods determined from occupancy schedules for the patient room 210. An occupancy schedule may refer to any data, listing, or other time-specification mechanism indicative of scheduling for the patient room 210 or relevant personnel that access the patient room 210 (e.g., the patient, medical staff, cleaning staff, visitors, etc.). FIG. 3 shows one example of an occupancy schedule stored by the patient information management system 311 through a patient treatment schedule 320 for a patient, which the disinfection environment tracking engine 108 may retrieve for a patient assigned to the patient room 210.

The UV light control engine 110 may analyze the patient treatment schedule 320 (or any other occupancy schedule) to determine occupied and unoccupied time periods for the patient room 210. For instance, the UV light control engine 110 may identify an assigned occupancy period from the patient information management system 311 during which a patient is assigned to the patient room 210 (e.g., via patient-to-room assignment data tracked by an ADT system or system module implemented by the patient information management system 311). During the assigned occupancy period, the UV light control engine 110 may extract time periods from the patient treatment schedule 320 during which the patient is scheduled for treatments or other medical activity outside of the patient room 210. The UV light control engine 110 may interpret any such scheduled time periods during which the patient is not scheduled to be present in the patient room 210 as unoccupied time periods for the patient room 210. Non-scheduled times may be interpreted by the UV light control engine 110 as occupied time periods during which the patient is scheduled or expected to be present in the patient room 210.

As illustrative example, the disinfection environment tracking engine 108 may access patient admission date/time data and a patient treatment schedule 320 from the patient information management system 311, specifically for the patient assigned to the patient room 210. The obtained patient information may indicate a patient admission time of 9:00 am and a CT scan scheduled for 1:00 pm-2:00 pm on the same day. Accordingly, the UV light control engine 110 may determine the time period from 9:00 am-1:00 pm as an occupied time period and the time period from 1:00 pm-2:00 pm as an unoccupied time period for the patient room 210 based on the accessed patient treatment schedule 320. In a similar manner, the UV light control engine 110 may parse or extract other unoccupied and occupied time periods from the patient treatment schedule 320.

The UV light control engine 110 may control operation of the UV light 220 in the patient room 210 according to the unoccupied time periods extracted from the patient treatment schedule 320. During the determined unoccupied time periods, the UV light control engine 110 may activate the UV light 220 to disinfect the patient room 210 and deactivate the UV light 220 during the determined occupied time periods in the patient treatment schedule 320.

While a patient treatment schedule 320 is provided as an example source (e.g., occupancy schedule) from which the UV light control engine 110 may determine unoccupied time periods for the patient room 210, other data sources may be likewise utilized to determine scheduled occupancy of the patient room 210. Other example sources include visitation hours to the patient room 210 (or the assigned patient), active visitations (e.g., when a visitor to the patient room 210 has been logged into a visitation system but not yet logged out), visitation schedules of medical staff (e.g., medical rounds or scheduled check-ins by nursing staff), cleaning staff schedules, etc., each for which the UV light control engine 110 may treat as an occupied time period for the room 210. For unoccupied time periods determined from any such sources, the UV light control engine 110 may activate the UV light 220 and deactivate the UV light 220 during determined occupied time periods.

As another example factor by which a building automation system 100 may control UV lighting, the UV light control engine 110 may account for an actual location of the patient, e.g., as tracked by real-time location data for the patient assigned to the patient room 210. Hospitals or other medical facilities may include real-time tracking capabilities for admitted patients or other personnel. Example location capture techniques include 802.11 triangulation from access points in a building, Bluetooth beaconing, infrared sensors positioned across the building to track patient movement, and ultrasound or ultra high-frequency wireless tracking systems.

In the example shown in FIG. 3, the hospital 200 includes the patient real-time location (RTL) system 312 that stores patient RTL data 330. Although shown separately in FIG. 3, the patient RTL system 312 may be implemented as a component or sub-system of the patient information management system 311.

The disinfection environment tracking engine 108 may access the patient RTL data 330 for a patient assigned to the patient room 210, and the UV light control engine 110 may control operation of the UV light 220 based on the accessed patient RTL data 330. For instance, the UV light control engine 110 may automate activation of the UV light 220 during an unoccupied time period of the patient room 210 determined from the patient treatment schedule 320. In such instances, the UV light control engine 110 may use the patient RTL data 330 (and additionally or alternatively use an occupancy status accessed from the occupancy sensor 211) to confirm that the patient is no longer present in the patient room 210 during the unoccupied time period. Put another way, the UV light control engine 110 may confirm, via the patient RTL data 330, that the patient is not present in the patient room 210 during determined unoccupied time periods and, in response, activate the UV light 220 to disinfect the patient room.

As another example use of the patient RTL data 330, the UV light control engine 110 may activate the UV light 220 when a patient is at least a threshold distance away from the patient room 210 and deactivate the UV light 220 otherwise. To illustrate, the UV light control engine 110 may enforce an activation criteria that activates the UV light 220 only when the patient is at least 10 feet (or any other configurable distance) from the patient room 210. Responsive to a determination that the patient is less than 10 feet from the patient room 210 (e.g., returning to the patient room 210 after a scheduled treatment), the UV light control engine 110 may deactivate the UV light 220.

As described above, the UV light control engine 110 may control operation of the UV light 220 to account for occupancy of the patient room 210. Actual or predicted (e.g., scheduled) occupancy may be determined in various ways, and the disinfection environment tracking engine 108 may access environment data, patient data, or any other data relevant or otherwise related to patient room occupancy.

The UV light control engine 110 may utilize any of the described environment or patient data alone to control UV light operation. For instance, the UV light control engine 110 may use one of the occupancy status data extracted from the occupancy sensor 211, the unoccupied time periods extracted from the patient treatment schedule 320, or the patient location information tracked by the patient RTL data 330 as a sole condition or factor in activation and deactivation of the UV light 220. Alternatively, the UV light control engine 110 may use any of the accessed environment or patient data in combination to set automated activations of the UV light 220. For scheduled unoccupied time periods as determined from treatment schedules or other data sources, the UV light control engine 110 may activate the UV light 220 upon confirmation that the patient room 210 is actually unoccupied, e.g., as confirmed via the occupancy sensor 211, the patient RTL data 330 or both. For occupied time periods in which the patient is not scheduled to be outside the patient room 210, the UV light control engine 110 may opportunistically activate the UV light when the occupancy sensor 211 or patient RTL data 330 indicates the patient has left the patient room 210 or the patient room 210 is otherwise unoccupied.

Other automated settings may likewise be applied by the UV light control engine 110 to operate the UV light 220. For instance, a user (e.g., a system administrator) may schedule preset times during which the UV light 220 is activated. Such preset scheduling may correspond to a disinfection cycle or cleaning schedule set up by a medical facility. The UV light control engine 110 may effectuate the preset schedules by interfacing with the UV light controller 230 to activate the UV light 220 during the scheduled disinfection times. During these scheduled disinfection times (or any other time the UV light 220 is activated), the UV light control engine 110 may override the activation based on a detected room occupancy, e.g., by immediately deactivating the UV light 220 responsive to a change in occupancy status as detected by the occupancy sensor 211, when the patient RTL data 330 indicates the patient is occupying the patient room 210, or is within a threshold distance from the patient room 210.

As yet another example, the UV light control engine 110 may control operation of the UV light 220 by activating the UV light 220 responsive to a patient discharge or transfer. For instance, the disinfection environment tracking engine 108 may obtain discharge/transfer data from the patient information management system 311, which may specify a time when the patient assigned to the patient room 210 will be or has been discharged. Responsive to such a discharge/transfer determination, the UV light control engine 110 may schedule a UV light activation for the patient room 210 subsequent to the patient discharge/transfer (e.g., immediately subsequent or subsequent by a configured timing offset). Similarly as described above, the UV light control engine 110 may override the scheduled UV light activations upon detecting the patient room 210 is not unoccupied.

In many of the examples described above, the UV light control engine 110 triggers activation or deactivation the UV light 220 to disinfect the patient room 210. As another feature, the UV light control engine 110 may control operation of the UV light 220 by setting any number of operation parameters of the UV light 220. For example, the UV light control engine 110 may calibrate the light intensity of the UV light 220, otherwise modulate between different light intensities, or otherwise configure any operation parameter of the UV light 220. Parameter control, UV light activation and deactivation, and other control of the UV light 220 may be specified through control instructions sent by the UV light control engine 110, e.g., the control instructions 350 shown in FIG. 3.

The UV light control engine 110 may configure operation of the UV light 220 according to a determined available disinfection period in which the patient room 210 is expected to or predicted to be unoccupied. The UV light control engine 110 may determine an available disinfection period based on accessed patient treatment schedules 320, for example, or according to any other schedule extraction techniques to identify preset times in which the patient is not scheduled to occupy the patient room 210. That is, the UV light control engine 110 may treat a determined unoccupied time period as an available disinfection period, though other ways to determine an available disinfection period are possible as well.

As another example of available disinfection period determination, the UV light control engine 110 may correlate a patient distance from the patient room 210 to a baseline (e.g., minimum) available disinfection period. The UV light control engine 110 may, for instance, convert a patient distance from the patient room 210 into a minimum available disinfection period based on the walking or transportation speed for a patient to return to the patient room 210. To provide a concrete illustration, the UV light control engine 110 may determine an available disinfection period of at least 45 seconds when the patient is at least 100 feet from the patient room 210. Various distance-to-timing translations may be used, for example based on tiered distance translations (e.g., 20-40 feet away=8 seconds of available disinfection period, 40-80 feet away=20 seconds of available disinfection period, etc.)

As yet another illustration, the UV light control engine 110 may identify a particular available disinfection period based on the patient reaching or being at a particular location, e.g., as determined from the patient RTL data 330. For instance, the patient RTL data 330 may indicate the patient has reached a particular medical facility or room that requires a threshold amount of time for treatment (e.g., a MRI or CT scanning room, surgery room, delivery room, intensive care unit, etc.). In such cases, the UV light control engine 110 may identify a correlated available disinfection period for the patient location, which may be specified in a correlation table or other configurable data structure.

The UV light control engine 110 may adjust, customize, optimize, or intelligently automate operation of the UV light 220 based on determined available disinfection periods. In some examples, the UV light control engine 110 may reduce the UV light intensity of the UV light 220 to reduce energy consumption during an available disinfection period of the patient room 210 (e.g., determined as an unoccupied time period) such that the UV light 220 is nonetheless effective to disinfect the patient room 210 during the available disinfection period.

In other examples, the UV light control engine 110 may deactivate the UV light 220 during the available disinfection period due to a disinfection cycle completing prior to the available disinfection period ending. Such a scenario may occur in which the patient is away from the patient room 210 for an extended period of time, upon which the UV light control engine 110 may reduce resource consumption and lighting costs by deactivating the UV light 220 once a sufficient amount of UV disinfection has occurred.

Another factor by which the UV light control engine 110 may activate or calibrate operation of the UV light 220 is patient medical conditions. Some examples of UV light control based on medical data of a patient are described next in FIG. 4.

Figure 4:
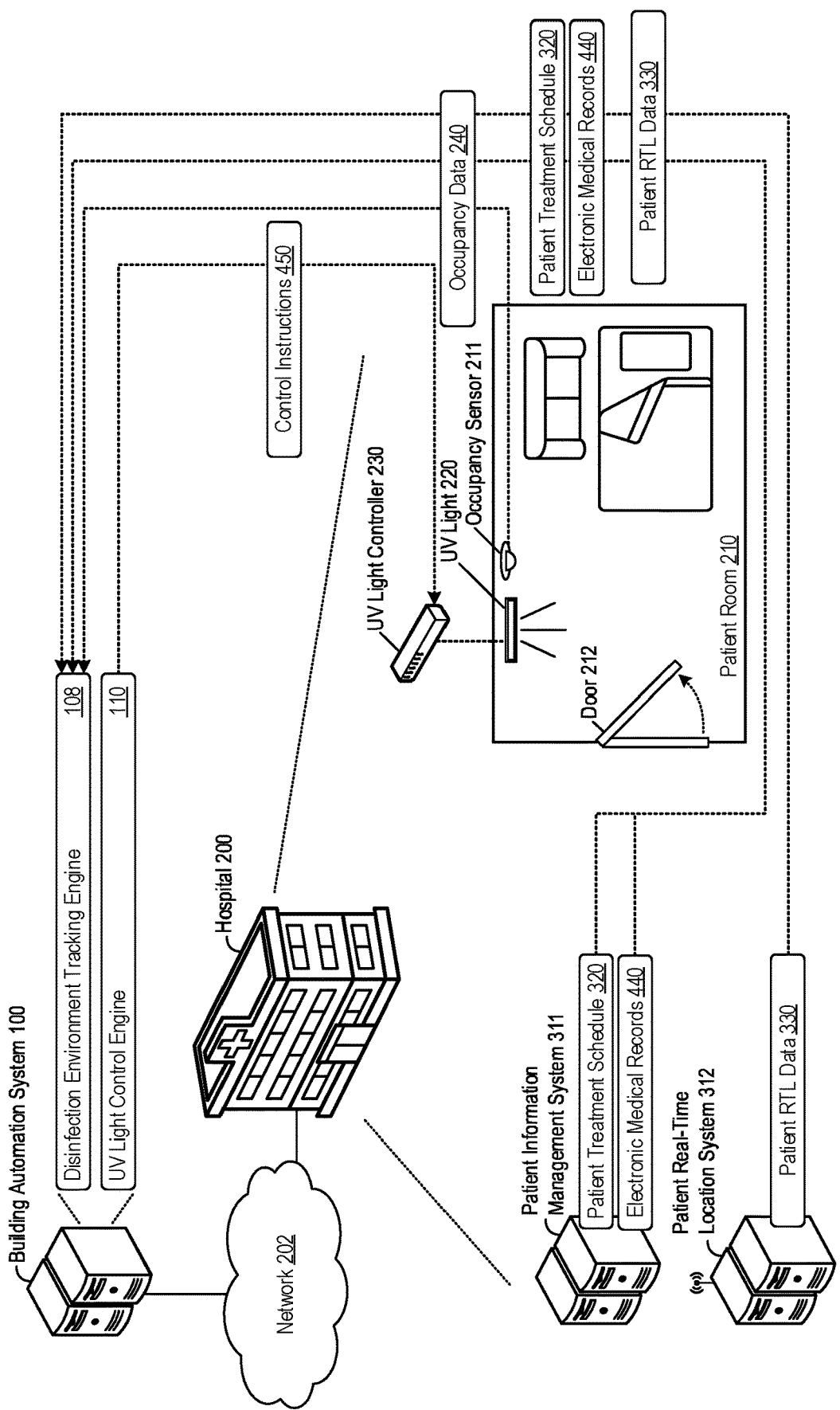
FIG. 4 shows an example of UV light control by a building automation system based on patient room data, real-time location data of a patient, and medical data of a patient.

FIG. 4 shows an example of UV light control by a building automation system based on patient room data, real-time location data of a patient, and medical data of a patient. In FIG. 4, the disinfection environment tracking engine 108 accesses medical data of a patient, through which the UV light control engine 110 may activate or calibrate operation of the UV light 220 to disinfect the patient room 210. Example medical data accessible by the disinfection environment tracking engine 108 includes the current medical conditions(s) of a patient, infection capabilities of medical conditions, disease treatment methods, patient medical history, and more.

In FIG. 4, the patient information management system 311 stores medical data in the form of electronic medical records 440 for a patient assigned to the patient room 210. The disinfection environment tracking engine 108 may retrieve the electronic medical records 440 for the patient and the UV light control engine 110 may adapt control of the UV light 220 for the patient room 210 based on the accessed electronic medical records 440.

In a general sense, the UV light control engine 110 may tailor UV light operation for the patient room 210 to specifically address particular medical conditions or disease capabilities the patient room 210 is exposed to. As particular examples, the UV light control engine 110 may account for a contagiousness level or disease spreading capabilities of medical conditions that afflict the patient of the patient room 210. The UV light control engine 110 may increase the UV light intensity or activation UV disinfection times of the UV light 220 for severe or highly contagious medical conditions (e.g., airborne pathogens or life-threatening bacteria) or reduce UV operation parameters for medical conditions of lesser severity or contagiousness level (e.g., common cold, or non-infectious medical conditions).

In some implementations, the UV light control engine 110 may access disinfection parameters for specific diseases, medical conditions, or ailments from medical databases. The center for disease control (CDC), research facilities, or other healthcare agencies may provide treatment recommendations or parameters for various medical conditions, and the building automation system 100 may access any such treatment parameters to calibrate the UV light 220. Such parameters may specify best-practices or recommended disinfection parameters, including UV light intensities and UV disinfection times to effectively eradicate infectious bacteria and diseases.

The UV light control engine 110 may determine a disinfection time (or active disinfection time), which may refer to a baseline or minimum time period to activate the UV light 220 to disinfect the patient room 210. Put another way, the UV light control engine 110 may determine the disinfection time as the required time period needed to effectively disinfect the patient room 210 through activation of the UV light 220. Determination of the disinfection time may be performed as a function of the UV light capabilities of the UV light 220 (e.g., maximum intensity), severity of a medical condition exposed to the patient room 210, length of time that the patient has occupied the patient room 210 prior to disinfection, and various other factors. The more severe the medical condition and the longer the patient has occupied the patient room 210 prior to UV light activation, the longer the disinfection time that the UV light control engine 110 may determine. Various weights may be applied to each factor in the disinfection time determination, which may be configurable based on UV disinfection goals (e.g., healthcare associated infections reduction, UV light costs, efficiency, patient traffic, etc.).

As one example, the UV light control engine 110 may determine a disinfection time for the patient room 210 based on a severity of the medical condition of the patient and a length of an occupied time period in an occupancy schedule (e.g., the patient treatment schedule 320) in which the patient occupies the patient room 210. The UV light control engine 110 may further identify an unoccupied time period in the occupancy schedule in which the patient does not occupy the patient room and activate the UV light 220 to disinfect the patient room 210 during the unoccupied time period responsive to a determination that a length of the unoccupied time period exceeds the determined disinfection time. When the determined disinfection time exceeds (i.e., is longer than) the unoccupied time for the patient room 210, the UV light control engine 110 may operate the UV light 220 with increased intensity or, alternatively, determine not to activate the UV light 220 at all (e.g., as a determination that the unoccupied time period is too short to effectively disinfect the patient room 210 and UV light activation would result in inefficient resource consumption).

When the UV light control engine 110 identifies a determined disinfection time is shorter than an unoccupied time period, the UV light control engine 110 may operate the UV light 220 in various ways. In some instances, the UV light control engine 110 may activate the UV light 220 for a length of time equal to the determined disinfection time, and deactivate the UV light 220 afterwards. Doing so may reduce resource consumption by turning off the UV light 220 after effective UV light disinfection has been achieved. In other instances, the UV light control engine 110 may reduce a light intensity of the UV light 220 to reduce energy consumption during the unoccupied time period of the patient room 210 such that the UV light 220 is nonetheless effective to disinfect the patient room for the length of the unoccupied time period based on the medical condition of the patient. Other calibration or activation options are possible as well. Such control of the UV light 220 may be effectuated by the UV light control engine 110 through the control instructions 450 generated and sent to the UV light controller 230.

Thus, the UV light control engine 110 may adapt operation of the UV light 220 to account various disinfection environment and patient-based factors. While some examples are described herein, the UV light control engine 110 may account for any number of additional or alternative factors in controlling the activation, deactivation, disinfection duration, and UV intensity of the UV light 220 in disinfecting the patient room 210.

Figure 5:
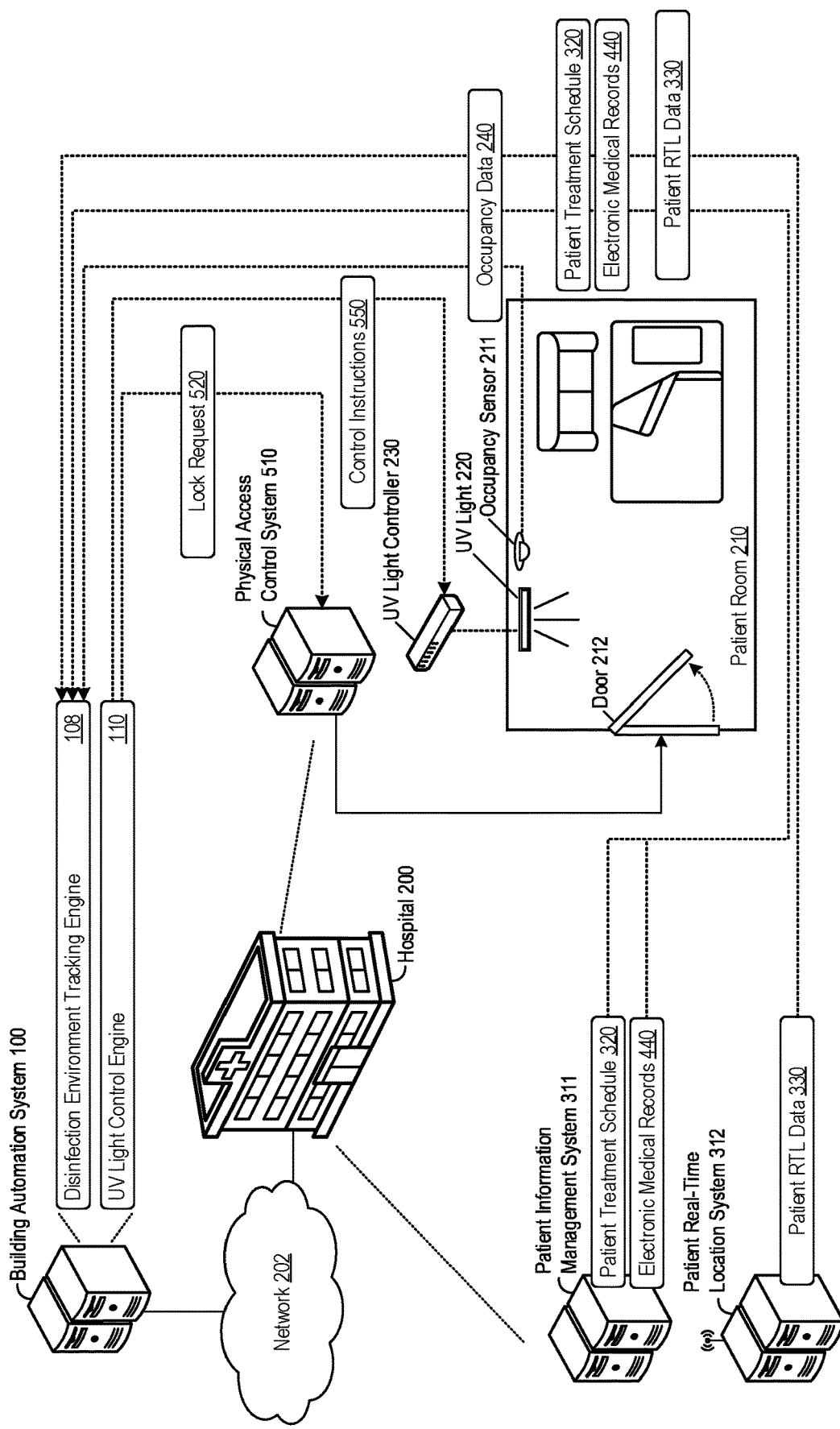
FIG. 5 shows an example of UV light control and room access control by a building automation system.

FIG. 5 shows an example of UV light control and room access control by a building automation system 100. As another feature of UV light control, the building automation system 100 may limit access to a disinfection environment undergoing UV light disinfection. In FIG. 5, the UV light control engine 110 may interface with the hospital access systems to control access to the patient room 210 during UV light operation to reduce or prevent inadvertent exposure to the UV light 220 when activated.

In particular, the hospital 200 shown in FIG. 5 includes a physical access control system 510. The physical access control system 510 may be any system, logic, hardware, or physical elements that control access to building spaces within the hospital 200. As such, the physical access control system 510 may support room lockdowns, gated entries, badge security, or support other access control mechanisms in the hospital 200. For the patient room 210, the physical access control system 510 may have access limitation capabilities to lock or unlock the door 212 of the patient room 210.

The UV light control engine 110 may limit access to the patient room 210 upon activation of the UV light 220. Prior to, concurrent with, or directly subsequent to activation of the UV light 220, the UV light control engine 110 may cause the physical access control system 510 to deny access to the patient room 210, doing so to prevent human exposure to UV light. In some examples, the UV light control engine 110 may send a lock request 520 to a physical access control system 510 to lock the door 212 of the patient room 210 when the UV light 220 is active to disinfect the patient room. In some instances, the UV light control engine 110 sends a one-sided lock request to the physical access control system 510 to deny exterior entry to the patient room 210 but allowing interior exiting from the patient room 210. Responsive to such a request, the physical access control system 510 may lock the door 212 from outside access but allow for exiting of the patient room 210 through the door 212, e.g., in case the patient or another person is located within the patient room 210 upon activation of the UV light 220.

In some instances, the UV light control engine 110 may issue an alarm warning prior to activation of the UV light 220. The alarm warning may cause an acoustic or visual warning to be issued in the patient room 210 prior to activation of the UV light 220, e.g., via an alarm system or sound system of the hospital 200. Upon deactivation of the UV light 220, the UV light control engine 110 may send an unlock request to the physical access control system 510. In some instances, the UV light control engine 110 sends the unlock request after a threshold amount of time has elapsed since deactivation of the UV light 220, providing another measure of safety. Accordingly, the building automation system 100 may provide various safety features to reduce or prevent human exposure to the UV light 220 during active UV disinfection periods. The building automation system 100 may do so in combination with intelligent control of the UV light 220 (e.g., as effectuated through control instructions 550) to disinfect various disinfection environments).

Figure 6:
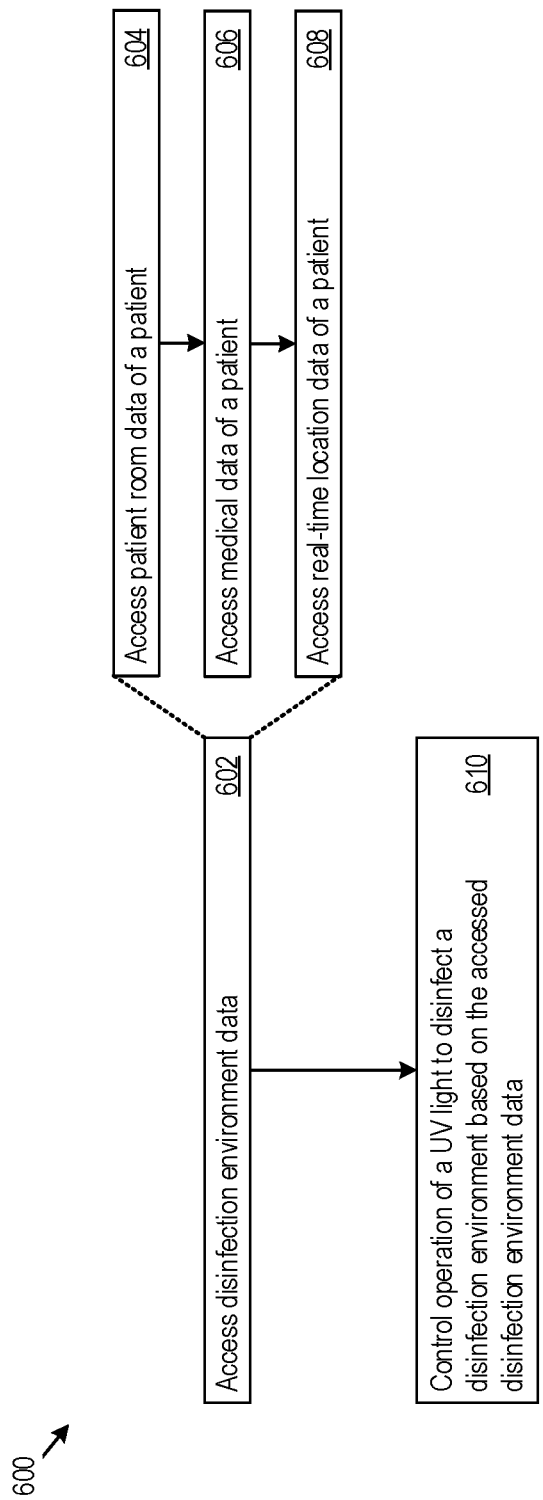
FIG. 6 shows an example of logic that a system may implement to support control of UV lights to disinfect patient rooms.

FIG. 6 shows an example of logic 600 that a system may implement to support control of UV lights to disinfect patient rooms. For example, the building automation system 100 may implement the logic 600 as hardware, executable instructions stored on a machine-readable medium, or as a combination of both. The building automation system 100 may implement the logic 600 through the disinfection environment tracking engine 108 and the UV light control engine 110, through which the building automation system 100 may perform or execute the logic 600 as a method to control UV lights for room disinfection. The following description of the logic 600 is provided using the disinfection environment tracking engine 108 and the UV light control engine 110 as examples. However, various other implementation options by the building automation system 100 are possible.

In implementing the logic 600, the disinfection environment tracking engine 108 may access disinfection environment data (602). The disinfection environment data may include any data relevant to a disinfection environment, whether it be a patient room or other space, as well as any other data that may impact UV light disinfection, such as medical data, occupancy time periods, and the like. For example, in accessing the access disinfection environment data, the disinfection environment tracking engine 108 may access patient room data of a patient (604), access medical data of the patient (606), and access real-time location data of the patient (608). In implementing the logic 600, the UV light control engine 110 may control operation of a UV light to disinfect a disinfection environment based on the accessed in disinfection environment data (610).

Figure 7:
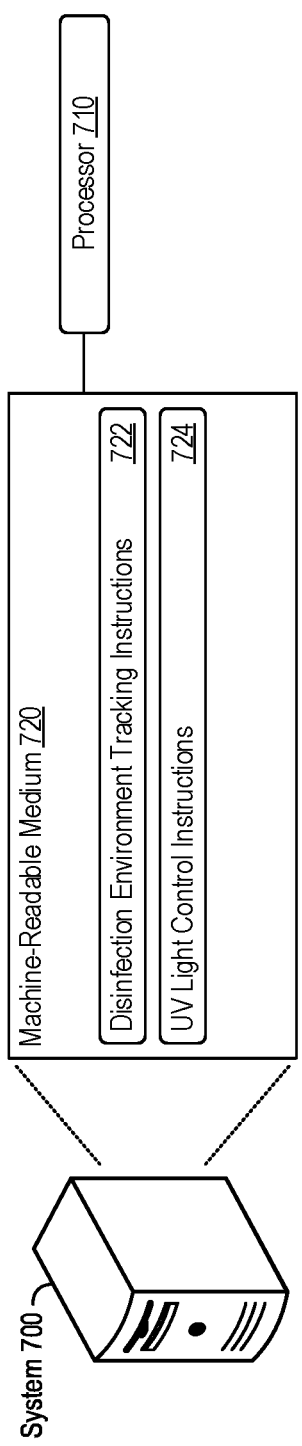
FIG. 7 shows an example of a system that supports control of UV lights to disinfect patient rooms or other disinfection environments.

FIG. 7 shows an example of a system that supports control of UV lights to disinfect patient rooms or other disinfection environments. The system 700 may include a processor 710, which may take the form of a single or multiple processors. The processor(s) 710 may include a central processing unit (CPU), microprocessor, or any hardware device suitable for executing instructions stored on a machine-readable medium. The system 700 may include a machine-readable medium 720. The machine-readable medium 720 may take the form of any non-transitory electronic, magnetic, optical, or other physical storage device that stores executable instructions, such as the disinfection environment tracking instructions 722 and the UV light control instructions 724 shown in FIG. 7. As such, the machine-readable medium 720 may be, for example, Random Access Memory (RAM) such as a dynamic RAM (DRAM), flash memory, spin-transfer torque memory, an Electrically-Erasable Programmable Read-Only Memory (EEPROM), a storage drive, an optical disk, and the like.

The system 700 may execute instructions stored on the machine-readable medium 720 through the processor 710. Executing the instructions may cause the system 700 (e.g., a building automation system) to perform any of the UV light control features described herein, including according to any of the features with respect to the building automation system 100, the disinfection environment tracking engine 108, the UV light control engine 110, or combinations thereof. For example, execution of the disinfection environment tracking instructions 722 by the processor 710 may cause the system 700 to access patient room data indicative of a state of a patient room of a patient, the patient room data including an occupancy schedule for the patient room that indicates an unoccupied time period during which the patient does not occupy the room and access medical data of the patient, the medical data of the patient specifying a medical condition of the patient.

Execution of the UV light control instructions 724 by the processor 710 may cause the system 700 to control operation of UV light to disinfect the patient room based on the patient room data and the medical condition of the data, including by calibrating the UV light to account for a length of the unoccupied time period and a severity of the medical condition of the patient.

The systems, methods, devices, and logic described above, including the building automation system 100, the disinfection environment tracking engine 108, and the UV light control engine 110, may be implemented in many different ways in many different combinations of hardware, logic, circuitry, and executable instructions stored on a machine-readable medium. For example, the building automation system 100, the disinfection environment tracking engine 108, the UV light control engine 110, or combinations thereof, may include circuitry in a controller, a microprocessor, or an application specific integrated circuit (ASIC), or may be implemented with discrete logic or components, or a combination of other types of analog or digital circuitry, combined on a single integrated circuit or distributed among multiple integrated circuits. A product, such as a computer program product, may include a storage medium and machine readable instructions stored on the medium, which when executed in an endpoint, computer system, or other device, cause the device to perform operations according to any of the description above, including according to any features of the building automation system 100, the disinfection environment tracking engine 108, the UV light control engine 110, or combinations thereof.

The processing capability of the systems, devices, and engines described herein, including the building automation system 100, the disinfection environment tracking engine 108, and the UV light control engine 110, may be distributed among multiple system components, such as among multiple processors and memories, optionally including multiple distributed processing systems or cloud/network elements. Parameters, databases, and other data structures may be separately stored and managed, may be incorporated into a single memory or database, may be logically and physically organized in many different ways, and may implemented in many ways, including data structures such as linked lists, hash tables, or implicit storage mechanisms. Programs may be parts (e.g., subroutines) of a single program, separate programs, distributed across several memories and processors, or implemented in many different ways, such as in a library (e.g., a shared library).

While various examples have been described above, many more implementations are possible.

The invention claimed is:

1. A system comprising:
   a disinfection environment tracking engine configured to:
   access patient room data indicative of a state of a patient room of a patient;
   access medical data of the patient, the medical data of the patient specifying a medical condition of the patient; and
   access real-time location data of the patient; and
   an ultra-violet (UV) light control engine configured to control operation of a UV light device based on the patient room data, the medical data of the patient, and the real-time location data of the patient, wherein the UV light control engine is configured to control the operation of the UV light device by determining a disinfection time for the patient room based on a severity of the medical condition of the patient and a length of an occupied time period in which the patient occupies the patient room.

2. The system of claim 1, wherein the patient room data comprises an occupancy schedule for the patient room specific to the patient; and
   wherein the UV light control engine is configured to further control the operation of the UV light device by:
   identifying an unoccupied time period in the occupancy schedule in which the patient does not occupy the patient room; and
   activating the UV light device to disinfect the patient room during the unoccupied time period responsive to a determination that a length of the unoccupied time period exceeds the determined disinfection time.

3. The system of claim 2, wherein the UV light control engine is further configured to control the operation of the UV light device by:
   activating the UV light device during the unoccupied time period responsive to a determination from the real-time location data that the patient is more than a threshold distance from the patient room; and
   deactivating the UV light device during the unoccupied time period responsive to a determination from the real-time location data that the patient is less than the threshold distance from the patient room.

4. The system of claim 1, wherein the disinfection environment tracking engine is configured to access the patient room data by obtaining an occupancy status of the patient room from an occupancy sensor in the patient room; and
   wherein the UV light control engine is configured to control the UV light device by deactivating the UV light device when the occupancy status indicates the patient room is occupied by the patient or another person.

5. The system of claim 1, wherein the UV light control engine is configured to control the UV light device based on the patient room data, the medical data of the patient, and the real-time location data of the patient by:
   reducing a UV light intensity of the UV light device to reduce energy consumption during an unoccupied time period of the patient room as determined from the patient room data or the real-time location data of the patient, such that the UV light device is nonetheless effective to disinfect the patient room during the unoccupied time period based on the medical condition of the patient.

6. The system of claim 1, wherein the UV light control engine configured to control the UV light device by:
   determining, from a patient information management system, an assigned occupancy period during which the patient is assigned to the patient room;
   determining, from the patient information management system, a patient treatment schedule for the patient during the assigned occupancy period that includes unoccupied time periods during which the patient is not present in the patient room; and confirming, via the real-time location data of the patient, that the patient is not present in the patient room during the unoccupied time periods and, in response, activating the UV light device to disinfect the patient room during the unoccupied time periods.

7. The system of claim 1, wherein the UV light control engine is further configured to send a lock request to a physical access control (PAS) system to lock a door of the patient room when the UV light device is active to disinfect the patient room.

* * * * *